(12) United States Patent
Kong et al.

(10) Patent No.: US 8,635,934 B2
(45) Date of Patent: Jan. 28, 2014

(54) MICROTOME

(76) Inventors: Jian-Qiang Kong, Greenville, NC (US);
George Y-H Kong, Greenville, NC (US)

(*) Notice: Subject to any disclaimer, the term of this patent is extended or adjusted under 35 U.S.C. 154(b) by 229 days.

(21) Appl. No.: 13/320,215

(22) PCT Filed: Aug. 25, 2010

(86) PCT No.: PCT/US2010/046665
§ 371 (c)(1),
(2), (4) Date: Nov. 11, 2011

(87) PCT Pub. No.: WO2011/034698
PCT Pub. Date: Mar. 24, 2011

(65) Prior Publication Data
US 2012/0055300 A1    Mar. 8, 2012

Related U.S. Application Data

(60) Provisional application No. 61/242,404, filed on Sep. 15, 2009.

(51) Int. Cl.
*B26D 7/06* (2006.01)

(52) U.S. Cl.
USPC ...... 83/42; 83/167; 83/169; 83/215; 83/915.5

(58) Field of Classification Search
USPC ........ 83/915.5, 13, 23, 42, 56, 412, 169, 170, 83/202, 215, 523, 527, 530, 167
See application file for complete search history.

(56) References Cited

U.S. PATENT DOCUMENTS

| | | | | |
|---|---|---|---|---|
| 325,722 A * | 9/1885 | Bausch | ............................ | 83/409 |
| 618,514 A * | 1/1899 | Low | ................................ | 83/466 |
| 708,298 A * | 9/1902 | Bausch | ............................ | 83/662 |
| 3,460,417 A * | 8/1969 | Johnson | .......................... | 83/111 |
| 3,467,075 A * | 9/1969 | Cary | ............................ | 125/13.01 |
| 3,667,330 A * | 6/1972 | Kobernick | ......................... | 83/98 |
| 3,799,029 A | 3/1974 | Cole et al. | | |
| 3,807,604 A | 4/1974 | Schaffer et al. | | |
| 4,239,963 A * | 12/1980 | August et al. | .............. | 73/514.26 |
| 4,377,958 A * | 3/1983 | Leighton | ....................... | 83/410.7 |
| 4,455,910 A | 6/1984 | Kraft et al. | | |
| D328,129 S | 7/1992 | Holbl | | |
| 5,226,335 A * | 7/1993 | Sitte et al. | ......................... | 83/74 |
| 5,461,953 A * | 10/1995 | McCormick | ...................... | 83/36 |

(Continued)

FOREIGN PATENT DOCUMENTS

| | | |
|---|---|---|
| DE | 202004007658 | 7/2004 |
| JP | 5-340851 | 12/1993 |
| JP | 11-304668 | 11/1999 |
| JP | 2005-077368 | 3/2005 |

*Primary Examiner* — Sean Michalski
(74) *Attorney, Agent, or Firm* — Richard C. Litman

(57) ABSTRACT

The microtome (10) includes a base (12) having a tank (14) filled with a bath (16) mounted thereon. A feeding mechanism (20) for feeding select amounts of specimen to be sectioned protrudes through the base (12) into the bath (16). A cutting mechanism (40) spans the tank (14) and includes a reciprocating carriage (42) above the feeding mechanism (20). The carriage (42) is disposed at an angle with respect to the direction of reciprocation and includes a vibrating blade (62) hanging down from the carriage (42). The combined motion of the carriage (42) and the vibrating blade (62) slices samples from the specimen extruded by the feeding mechanism (20), which permits consistent and uniformly thick samples with minimal surface irregularities, especially for large specimens. A controlling mechanism (80) coordinates operation of the feeding mechanism (20) and the cutting mechanism (40).

13 Claims, 3 Drawing Sheets

(56) References Cited

U.S. PATENT DOCUMENTS

| | | | |
|---|---|---|---|
| 5,671,648 A | 9/1997 | Dern | |
| 5,713,255 A | 2/1998 | Izvozichikov | |
| 6,041,686 A * | 3/2000 | Lihl et al. | 83/628 |
| 6,105,483 A * | 8/2000 | Takeda | 83/881 |
| 6,651,538 B2 * | 11/2003 | Tamura et al. | 83/575 |
| 6,871,572 B1 | 3/2005 | Haussler et al. | |
| 7,146,894 B2 * | 12/2006 | Hendrick et al. | 83/703 |
| 7,146,895 B2 * | 12/2006 | Kong et al. | 83/705 |
| 7,703,368 B2 | 4/2010 | Lang et al. | |
| 8,109,184 B2 * | 2/2012 | Kong et al. | 83/13 |
| 2006/0086221 A1 | 4/2006 | Kong et al. | |
| 2007/0053057 A1 * | 3/2007 | Zust et al. | 359/368 |
| 2007/0199418 A1 * | 8/2007 | Ito | 83/13 |
| 2008/0072722 A1 | 3/2008 | Tanki et al. | |
| 2010/0000383 A1 * | 1/2010 | Koos et al. | 83/22 |
| 2012/0055300 A1 * | 3/2012 | Kong et al. | 83/19 |

* cited by examiner

MICROTOME

CROSS-REFERENCE TO RELATED APPLICATION

This application is a 371 of PCT/US2010/046665, filed Aug. 25, 2010, which claims the benefit of U.S. Provisional Patent Application Seri. No. 61/242,404, filed Sep. 15, 2009.

BACKGROUND OF THE INVENTION

1. Technical Field

The present invention relates to research and medical devices, more specifically to a sliding and vibrating microtome for sectioning large diameter tissue specimens.

2. Background Art

Much of the modern research and medical examinations require biological samples for analysis. These samples are typically furnished by microtomes that make very thin slices or sections of tissue specimens, usually in μm, to be prepared on a slide. For best results, the sliced samples should have uniform thickness and minimal or no surface irregularities. Otherwise, any of these types of irregularities could potentially lead to, inter alia, difficult comparative studies between samples from the same specimen and poor imaging.

Various microtomes have been in existence for sectioning samples. Some utilize a blade mounted on a sliding carriage to slice or section off a sample from an extruded specimen embedded in a gel substrate, e.g., agarose. Others utilize a vibrating blade, i.e., a vibratome, to perform the same. A common issue with these microtomes is that most cannot accommodate large specimens without compromising the quality of the sections. Either the design limitations of the prior microtomes necessitate specimen samples to be small and/or the cutting mechanism cannot insure uniform thickness of the sliced sample or prevent undulations of the sliced surface if the specimen is too large, the latter being more prevalent with vibratory blades having oscillations in more than one plane or in a non-parallel plane with respect to the cutting plane.

Another issue is that most microtomes include a cryostat or refrigeration unit to keep the specimen cold as required for certain specimens and the required analysis. However, if a large specimen is to be sectioned, then the refrigeration unit must be sized or configured accordingly which may increase the cost and maintenance for the unit. The inclusion of a refrigeration unit alone incurs substantial costs especially since they have to be meticulously controlled and monitored. In light of the above, it would be a benefit in the art of research devices to provide a microtome that can section large diameter specimens with consistent quality and relative economy.

Thus, a microtome solving the aforementioned problems is desired.

DISCLOSURE OF INVENTION

The microtome includes a base with a tank filled with a bath mounted thereon. A feeding mechanism for feeding select amounts of specimen to be sectioned protrudes through the base into the bath. A cutting mechanism spans the tank and includes a reciprocating carriage above the feeding mechanism. The carriage is disposed at an angle with respect to the direction of reciprocation and includes a vibrating blade hanging down from the carriage. The combined motion of the carriage and the vibrating blade slices samples from the specimen extruded by the feeding mechanism, which permits consistent and uniformly thick samples with minimal surface irregularities, especially for large specimens. A controlling mechanism coordinates operation of the feeding mechanism and the cutting mechanism.

These and other features of the present invention will become readily apparent upon further review of the following specification and drawings.

BRIEF DESCRIPTION OF THE DRAWINGS

Similar reference characters denote corresponding features consistently throughout the attached drawings.

BEST MODES FOR CARRYING OUT THE INVENTION

Figure 1:
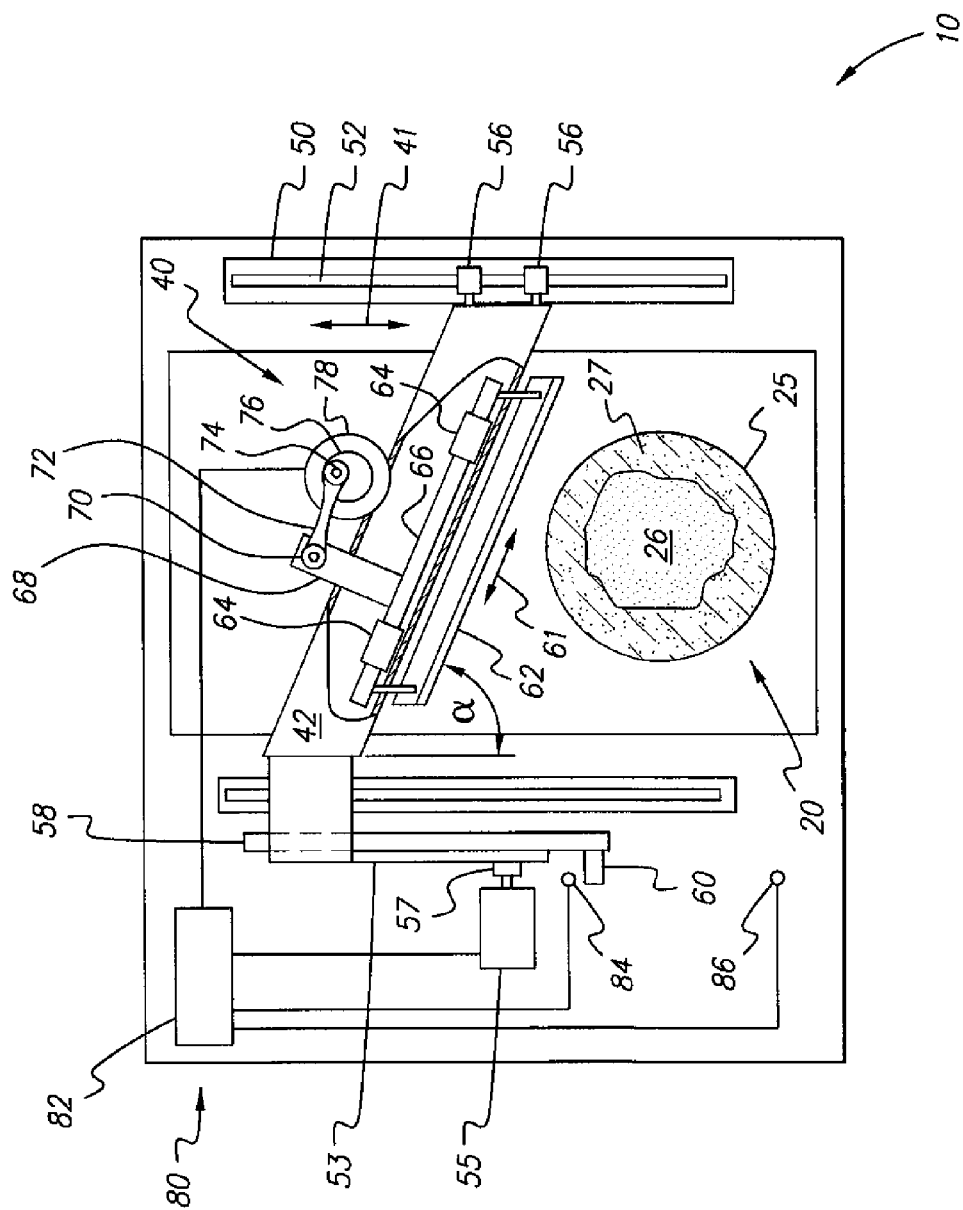
FIG. 1 is a diagrammatic top view of a microtome according to the present invention.
Figure 2:
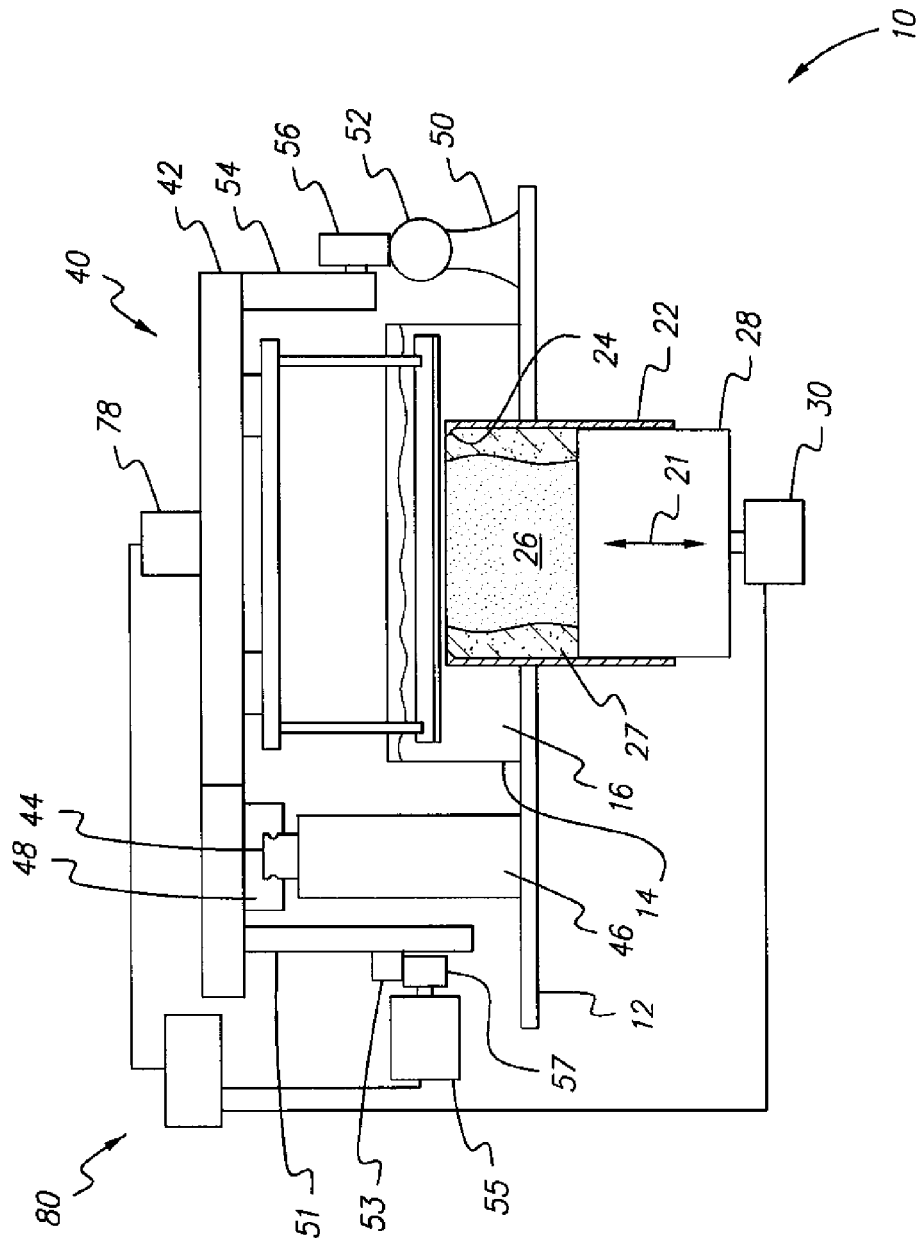
FIG. 2 is a diagrammatic front view of the microtome in FIG. 1, shown with the specimen feed in section.
Figure 3:
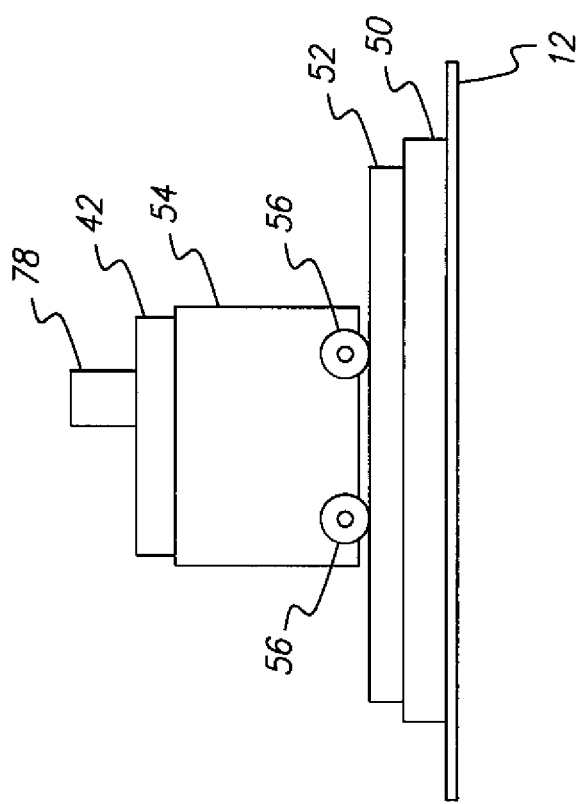
FIG. 3 is a diagrammatic side view of the sectioning station on the microtome.

The present invention relates to a microtome, generally referred to in the drawings by reference number 10, configured to section samples from a large diameter specimen with consistent quality and uniformity of thickness. As shown in FIGS. 1-3, the microtome 10 includes a base 12 upon which a buffer or wash tank 14 is disposed. A feeding mechanism 20 for incremental feeding of a specimen to be cut, sliced or sectioned is immersed in the bath or buffer solution or liquid 16. The bath 16 allows for temporary storage of the cut samples in a protective environment for further processing, and the bath 16 also helps to lubricate the cutting blade of the microtome 10. A cutting mechanism 40 for sectioning the desired portion of the specimen and a control mechanism 80 for controlling the feeding and cutting processes are both operatively disposed on the base 12.

The feeding mechanism 20 includes a cylindrical or tubular feed housing 22 passing through the base 12 into the tank 14. The feed housing 22 encloses a specimen 26 that has been prepared for sectioning by being embedded with a substrate 27. The substrate 27 is usually a gelatinous material made from agarose or derivatives thereof. One end of this specimen aggregate is attached to one end of a pusher, plunger or piston 28 with an adhesive or similar means. The term "specimen aggregate" herein is being used to refer to the combined mass of material comprising the specimen 26 and the substrate 27. The other end of the pusher 28 is operatively connected to a stepper motor 30. Operation of the stepper motor 30 displaces the pusher 28 in the direction indicated by arrow 21 to thereby feed a desired amount of to be cut specimen 26, i.e., the other end of the specimen 26, through a feed opening 25 on the feed housing 22. The stepper motor 30 permits highly accurate and consistent incremental feeding of the specimen 26 for subsequent sectioning, which contributes to uniformity in thickness of the cut samples.

The feed housing 22 also includes a circular compression lip 24 at the feed end of the housing 22. The compression lip 24 may be a beveled edge that extends from the interior wall of the feed housing 22 towards the opening 25. As the specimen 26 exits the opening 25 while being fed by the pusher 28, the compression lip 24 restricts movement and compresses the mass of the specimen aggregate. This stabilizes and clamps the specimen aggregate to better counteract the cutting forces from the cutting mechanism 40 during the cutting operation. In this manner, incidences of irregular cut surfaces or contours can be drastically reduced or prevented.

The cutting mechanism 40 includes a carriage, beam or bridge 42 spanning more than the width of and above the tank 14. The carriage 42 is slidably supported on first and second rails 44, 52 on respective sides of the carriage 42 and reciprocates thereon as indicated by arrow 41.

The first side of the carriage 42 includes a race, channel, follower or linear bearing 48 depending from the bottom of the carriage 42. The linear bearing 48 includes a groove having a shape that mates with the shape of the first rail 44. In the exemplary embodiment, the first rail 44 has a substantially I-beam shape in cross section. This dovetail-like join between the linear bearing 48 and the first rail 44 insures that the movement of the carriage 42 is restricted along the length of the first rail 44. The first rail 44, in turn, is supported on an upstanding first support or stand 46 disposed on the base 12. Since the microtome 10 is a high precision instrument, it is preferable that the linear bearing 48 and the first rail are similar in capability. Various different linear bearing and rail combinations may be used as long as they can facilitate precise, restricted movement along the reciprocating direction, i.e., no undesirable movement in a perpendicular direction with respect to the reciprocating direction.

The second side of the carriage 42 includes a depending bearing support plate or beam 54 supporting a pair of rotary bearings 56. The rotary bearings 56 ride on the second rail 52. Unlike the first rail 44, the second rail 52 may be an elongate circular rod that provides tangential support for the rotary bearings 56 even when lateral shifts of the bearings 56 may occur during travel. The second rail 52, in turn, is supported on an upstanding second support or stand 50 disposed on the base 12. The second stand 50 is also shorter than the first stand 46.

The middle section of the carriage 42 includes a blade holder 66 slidably mounted on linear bearings 64. The blade holder 66 may be a rectangular frame hanging below the carriage 42 with a cutting knife or blade 62 mounted at the distal end from the linear bearings 64. The cutting blade 62 is disposed at a height close to but not co-planar with the opening 25.

To cut or section a sample from the tissue 26 and substrate 27, the cutting mechanism 40 utilizes a combination of the reciprocating movement of the carriage 42 and a vibratory reciprocation of the cutting blade 62, the vibrating direction indicated by arrows 61. In that regard, the microtome 10 includes a reciprocating mechanism for the carriage 42 and a vibration mechanism for the cutting blade 62.

As shown in FIGS. 1 and 2, the reciprocating mechanism includes a mounting plate 58 disposed on the first side of the carriage 42 and laterally spaced from the first rail 44. A rack 53 is mounted on the outer side of the mounting plate 58 with the teeth thereof being disposed at the bottom of the rack 53. A pinion 57 extends from a motor 55 and meshes with the rack 53. Thus, operation of the motor 55 rotates the pinion 57, which in turn forces the rack 53 to move in the reciprocating directions indicated by arrows 41. Due to the accuracies required for sectioning samples and the need to control the cutting rate, the motor 55 is preferably reversible and variable speed.

As shown in FIGS. 1-3, the vibration mechanism for the cutting blade 62 includes one end of a connector arm or beam 68 attached to the blade holder 66. The connector arm 68 is preferably made from relatively flexible, springy and/or resilient material, so that the connector arm 68 will better absorb the abrupt changes of momentum compared to a stiff beam or structure. One end of a crank arm 72 is connected to a bearing 70 on the other end of the connector arm 68 while the other end of the crank arm 72 is rotatably attached to an eccentric wheel 76 at bearing 74. The crank arm 72 is also preferably made from flexible, springy, and/or resilient material for the reasons noted above. A motor 78 rotates the eccentric wheel 76. Due to the amount of control required to obtain consistent and uniform thickness samples, the motor 78 is preferably reversible and/or variable speed. To vibrate the blade 62, the rotation of the eccentric wheel 76 via the motor 78 causes the crank arm 72 to push and pull the connector 68 in the direction indicated by arrows 61. This in turn reciprocates or vibrates the blade 62.

While the combined movements of the carriage 42 and the blade 62 alone will slice samples well, this may not be satisfactory when cutting relatively large diameter tissue specimens. More care must be exercised when cutting larger specimens due to the larger area to be cut. To facilitate, the middle section of the carriage 42 is disposed at an acute angle α as shown in FIG. 1, which accounts for the substantially parallelogram shape of the carriage 42. With this configuration, the angle of incidence between the sample aggregate and the cutting edge of the blade 62 is at the angle α rather than perpendicular as the carriage 42 reciprocates across the opening 25. As a result of the angular orientation, the cutting action is gradual across substrate 27 and the tissue specimen 26, which reduces the chances for irregular cut surfaces that can exist with more abrupt cutting forces acting on the specimen aggregate. Moreover, the linear movement of the carriage 42 and the vibratory movement of the blade 62 are limited to a plane in the x-y coordinates as viewed in FIG. 1. Any z-axis movement, i.e., up and down, of the blade 62 is prevented by the linear bearing 48 and the linear bearings 64, which insures that the blade 62 will not cause undulations on the cut surface. Furthermore, the length of the blade 62 is greater than the diameter of the specimen to be but. The combination of these factors results in more consistent uniform thickness of cut samples with minimal to no surface irregularities, especially for large specimens.

All of the operations of the microtome 10 are coordinated by the control mechanism 80. The control mechanism 80 includes a control unit 82 that communicates with the motor 30 to control the incremental feed of the specimen aggregate, the motor 55 to control the rate and direction of carriage movement, and the motor 78 to control the speed and direction of vibration. Moreover, the control mechanism 80 includes a detectable element 60 attached to one end of the mounting plate 58 and travels between a first sensor 84 and a second sensor 86 as the carriage 42 reciprocates. The detectable element 60 is preferably a magnet but any object that can be sensed by the first and second sensors 84, 86 are viable alternatives. The first and second sensors 84, 86 are preferably Hall-Effect or proximity sensors that can detect the magnetic strength of the magnet 60, and thereby accurately determine the exact position of the carriage 42. Other types of position sensors such as laser based sensors, rotary encoders, etc. may also be used for determining the position.

The following describes how to use the microtome 10. To section a large diameter specimen, the user mounts the specimen aggregate of tissue specimen 26 and substrate 27 onto the pusher 28 via adhesives. The stepper motor 30 is actuated to move the pusher 28 upward a desired amount. This causes the specimen aggregate to extrude from the opening 25 of the feed housing 22 and be compressed by the compression lip 24. The motor 78 is actuated to vibrate the blade holder 66 and blade 62. Then the motor 55 is activated to move the carriage 42 along the first and second rails 44, 52. This movement causes the blade 62 to traverse across the extruded specimen 26 and substrate 27 at a controlled rate resulting in a sliced sample. The sliced sample is left to float in the bath 16. With this arrangement, no freezing of the sample is required.

It is to be understood that the present invention is not limited to the embodiments described above, but encompasses any and all embodiments within the scope of the following claims.

We claim:

1. A microtome, comprising:
   a base;
   a tank disposed on the base, the tank being adapted for filling with a bath for sliced samples;
   a feeding mechanism for feeding select amounts of specimen to be sliced, the feeding mechanism extending through the base into the tank, the feeding mechanism having a housing adapted for holding the specimen;
   a movable cutting mechanism adapted for slicing samples from the specimen fed by the feeding mechanism; the cutting mechanism spanning above the feeding mechanism; the cutting mechanism having a reciprocating carriage movable in a direction toward and away from the feeding mechanism, and having a blade disposed at an acute angle with respect to the reciprocating direction, the blade vibrating along the acute angle; and
   a control mechanism for coordinating operations of the feeding mechanism and the cutting mechanism;
   wherein the combined movements of the carriage and the reciprocating blade minimize cut surface irregularities to produce sliced samples of uniform thickness.

2. The microtome according to claim 1, wherein said feeding mechanism comprises:
   an elongated tubular housing adapted for holding the specimen to be sliced, the tubular housing having a specimen feed end defining an opening for the specimen to be fed through;
   a pusher disposed inside the tubular housing at the end of the tubular housing opposite the specimen feed end, the pusher having a surface adapted for supporting the specimen; and
   a motor operatively connected to the pusher for positively moving the pusher and thereby exposing a select amount of specimen to be sliced through the opening.

3. The microtome according to claim 2, further comprising a compression lip at the opening in the specimen feed end for compressing the specimen as the specimen exits the opening to thereby clamp and stabilize the exposed specimen for slicing.

4. The microtome according to claim 3, wherein said compression lip comprises a circular, beveled edge extending from an interior wall of said tubular housing towards the opening.

5. The microtome according to claim 1, wherein said carriage being disposed at said acute angle, said carriage having a bottom, a middle section and first and second opposing ends, said cutting mechanism comprises:
   a vibrating mechanism disposed on the middle section for vibrating said blade;
   a first rail slidably supporting the first end of said carriage;
   a second rail slidably supporting the second end of said carriage; and
   a reciprocating mechanism for moving said carriage toward and away from said feeding mechanism.

6. The microtome according to claim 5, wherein said vibrating mechanism comprises:
   an elongated blade holder having a first end disposed in the middle section of said carriage and an opposite end holding said blade;
   at least one linear bearing attached to the first end of the blade holder to confine and smooth reciprocating movement of the blade holder;
   a connector arm attached to the first end of the blade holder, the connector arm having a bearing at one end;
   an eccentric wheel;
   a crank arm having one end connected to the bearing on the connector arm and the other end connected to the eccentric wheel; and
   a motor for rotating the wheel;
   wherein rotation of the eccentric wheel causes the crank arm to reciprocate the connector arm and thereby vibrate the blade holder.

7. The microtome according to claim 6, wherein said connector arm and said crank arm are made from resilient material to compensate vibratory forces acting thereon.

8. The microtome according to claim 5, further comprising:
   a first stand mounted on said base, the first stand having a height, said first rail being disposed on top of the first stand and having a cross-sectional shape;
   a first bearing extending from the bottom of said carriage, the first bearing having a channel defining a shape corresponding to the shape of said first rail, the first bearing being slidable along said first rail;
   a second stand mounted on said base, the second stand having a height less than the first stand, said second rail being disposed on top of the second stand, said second rail being an elongate circular rod;
   a support beam extending from the bottom of said carriage at the second end of said carriage; and
   a set of second bearings supported from the support beam, the second bearings being rotatably slidable on said second rail.

9. The microtome according to claim 8, wherein said set of second bearings comprises a pair of rotary bearings.

10. The microtome according to claim 5, wherein said reciprocating mechanism for moving said carriage comprises:
    a mounting plate disposed on the first side of said carriage, the mounting plate being laterally spaced from said first rail and having an outer side;
    a rack mounted on the outer side of the mounting plate;
    a pinion meshed with the rack; and
    a reversible motor connected to the pinion to rotate the pinion;
    wherein rotation of the pinion by the reversible motor forces the rack, and thereby said carriage, to reciprocate.

11. The microtome according to claim 1, wherein said control mechanism comprises:
    a control unit communicating with said feeding mechanism and said cutting mechanism;
    a detectable element attached to one end of said carriage; and
    spaced first and second sensors operatively connected to the control unit, the first and second sensors sensing the position of the detectable element and thereby said carriage.

12. The microtome according to claim 11, wherein said detectable element comprises a magnet.

13. A method of using a microtome to section large specimens comprising the steps of:
    providing a tank with a bath for sliced samples;
    providing a feeding mechanism extending into the tank;
    attaching a specimen onto the feeding mechanism with adhesive;

embedding the specimen with agarose gelatin within the feeding mechanism to thereby form a specimen aggregate;

feeding a select amount of specimen aggregate through an opening in the feeding mechanism;

compressing the select amount of specimen aggregate as the specimen aggregate exits the opening to clamp and stabilize the specimen aggregate;

providing a cutting mechanism having a reciprocating carriage and a vibrating blade, the carriage being movable in a direction toward and away from the feeding mechanism and disposed at an acute angle with respect to the direction of movement;

slicing a sample from the specimen aggregate by moving the carriage across the opening; and providing a control mechanism for coordinating the steps of feeding and slicing.

\* \* \* \* \*